United States Patent [19]
Gordon

[11] Patent Number: 5,669,923
[45] Date of Patent: Sep. 23, 1997

[54] ANTERIOR CAPSULOTOMY DEVICE AND PROCEDURE

[76] Inventor: Mark G. Gordon, 615 Orchid, Corona Del Mar, Calif. 92625

[21] Appl. No.: 593,532

[22] Filed: Jan. 24, 1996

[51] Int. Cl.$^6$ .................................................. A61B 17/32
[52] U.S. Cl. ............................ 606/170; 606/171; 604/22
[58] Field of Search .................... 606/107, 160, 606/161, 162, 166, 169, 170, 171, 182, 168; 604/22

[56] References Cited

U.S. PATENT DOCUMENTS

| | | | |
|---|---|---|---|
| 3,606,878 | 9/1971 | Kellogg, Jr. | 606/171 |
| 3,818,913 | 6/1974 | Wallach | 128/305 |
| 3,967,377 | 7/1976 | Wells | 606/170 |
| 3,994,297 | 11/1976 | Kopf | 606/107 |
| 4,517,977 | 5/1985 | Frost | 128/305 |
| 4,577,629 | 3/1986 | Martinez | 606/171 |
| 4,662,869 | 5/1987 | Wright | 604/22 |
| 4,674,502 | 6/1987 | Imonti | 128/305 |
| 4,696,298 | 9/1987 | Higgins et al. | 128/305 |
| 4,705,035 | 11/1987 | Givens | 128/303 R |
| 4,706,669 | 11/1987 | Schlegel | 606/107 |
| 4,750,491 | 6/1988 | Kaufman et al. | 128/305 |
| 4,796,623 | 1/1989 | Krasner et al. | 128/305 |
| 4,909,249 | 3/1990 | Akkas et al. | 604/22 |
| 4,911,161 | 3/1990 | Schechter | 606/107 |
| 4,986,827 | 1/1991 | Akkas et al. | 606/107 |
| 4,997,437 | 3/1991 | Griehaber | 606/166 |
| 5,011,498 | 4/1991 | Krumeich et al. | 606/166 |
| 5,019,035 | 5/1991 | Missirlian et al. | 604/22 |
| 5,084,059 | 1/1992 | Metzger | 606/166 |
| 5,234,436 | 8/1993 | Eaton et al. | 606/107 |
| 5,250,065 | 10/1993 | Clement et al. | 604/22 |
| 5,261,923 | 11/1993 | Soares | 606/166 |
| 5,285,795 | 2/1994 | Ryan et al. | 606/170 |

OTHER PUBLICATIONS 1 page document entitled Sever the Ties that Bind; Visitec Steve Charles, MD., "Vitreous Microsurgery"; pp. 25–41 1993.

Primary Examiner—Robert A. Hafer
Assistant Examiner—Justine R. Yu
Attorney, Agent, or Firm—Stetina Brunda Garred & Brucker

[57] ABSTRACT

A device for performing an anterior capsulotomy procedure has an elongate tubular member with an opening formed near the distal end thereof. A cutter is movably disposed within the tubular member and has a blade formed thereon. A vacuum port is in fluid communication with the lumen of the tubular member. An actuator effects movement of the cutter so as to move the blade across the opening. The opening is configured to draw in a portion of a capsule when a vacuum is applied to the vacuum port such that the cutter forms a generally circular cut of a predetermined size in the capsule when the actuator is actuated.

23 Claims, 6 Drawing Sheets

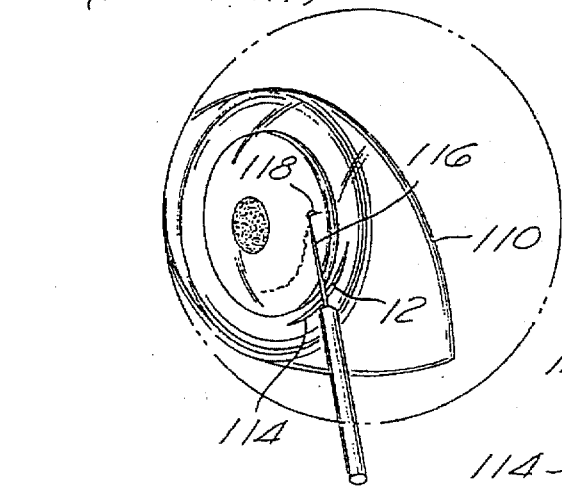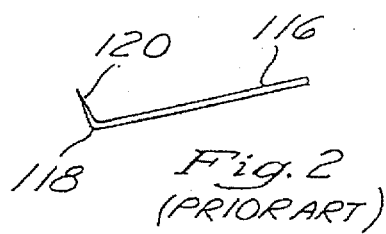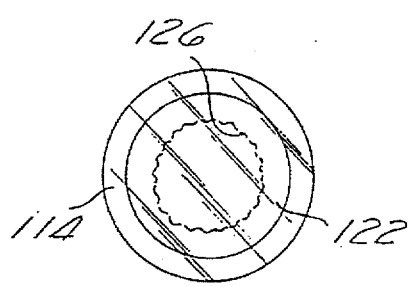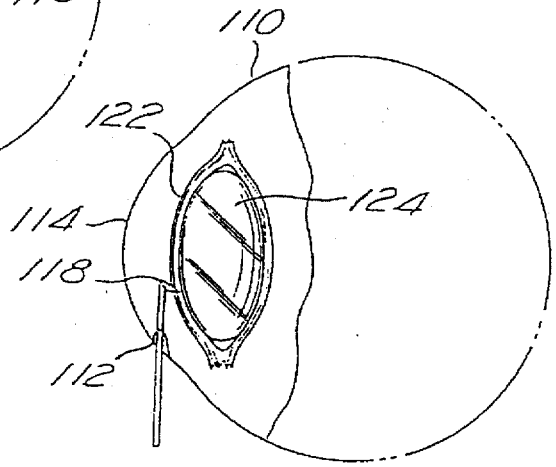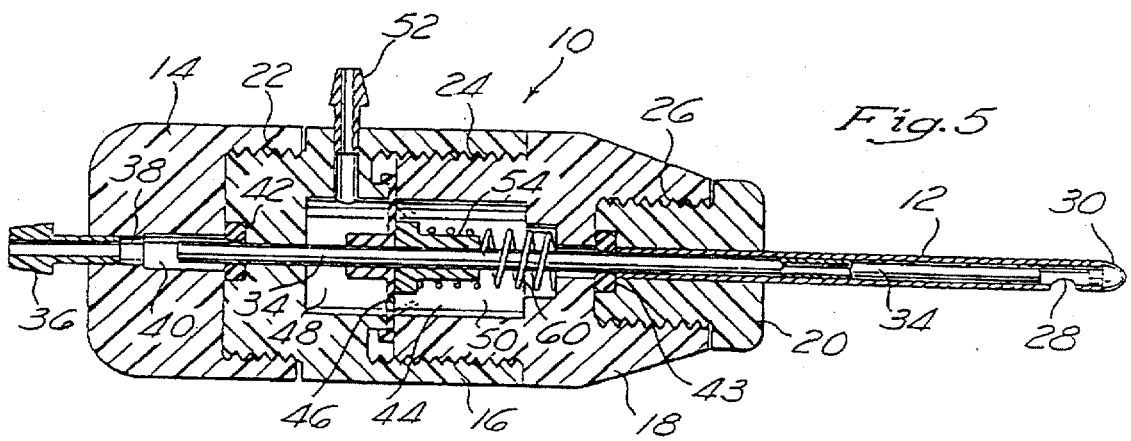

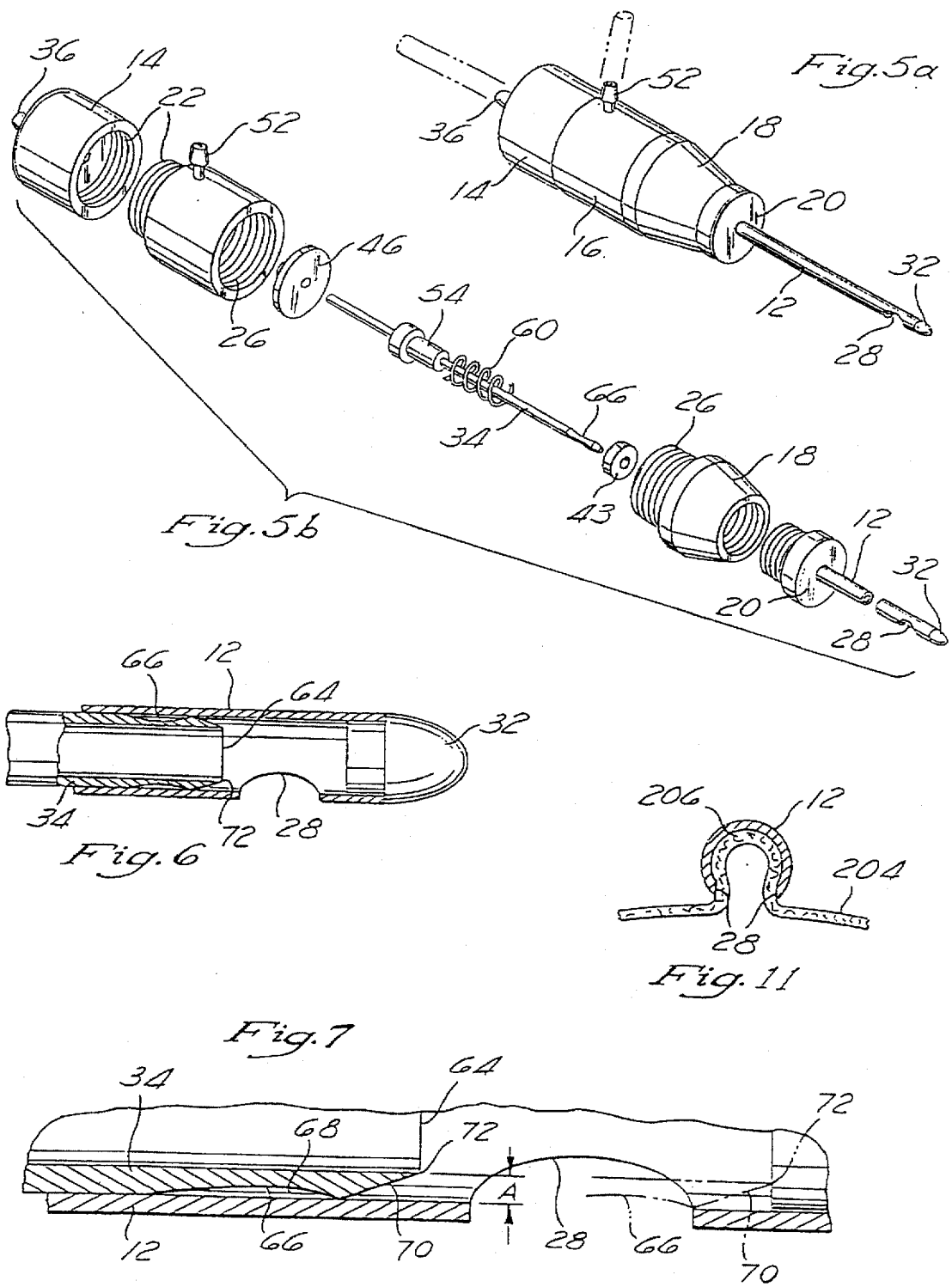

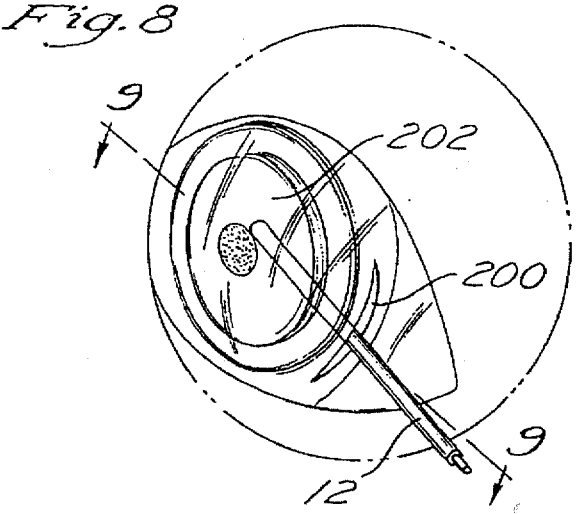
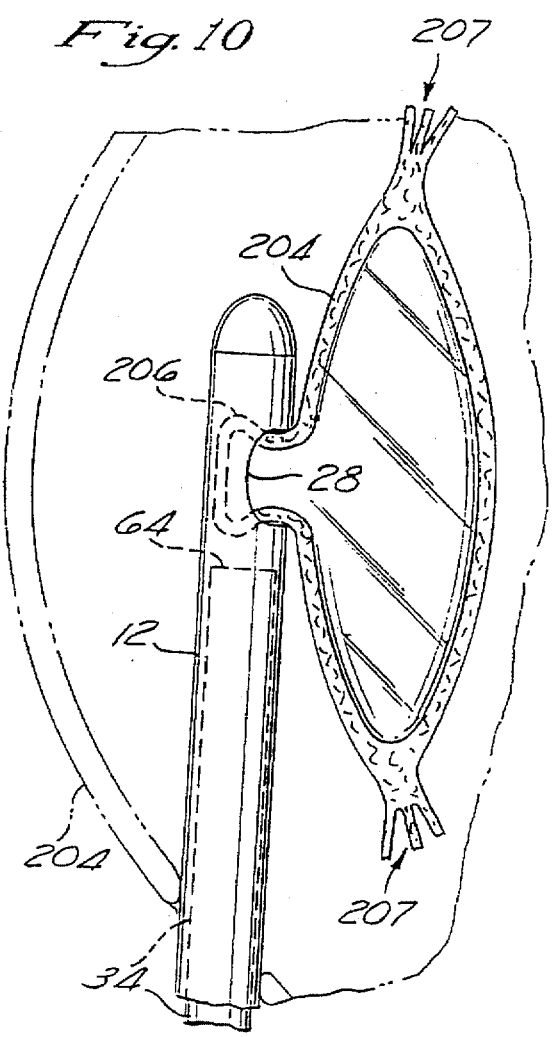
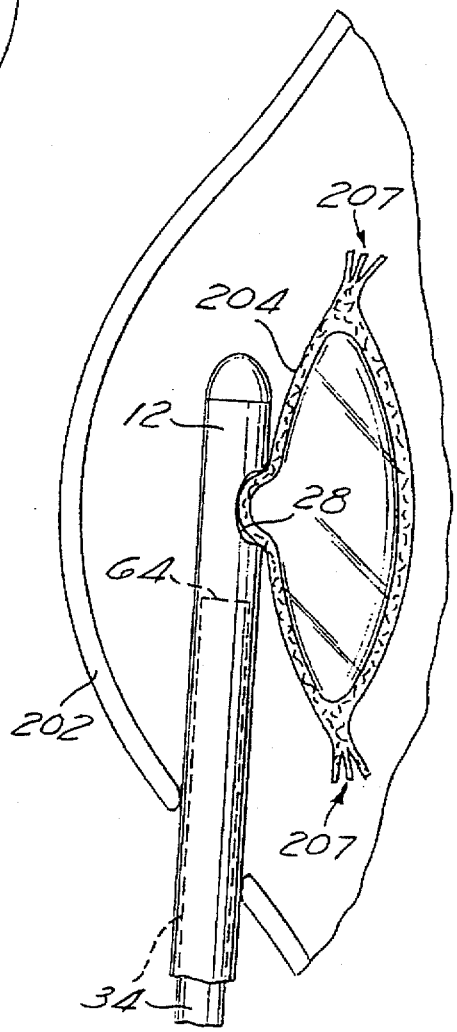
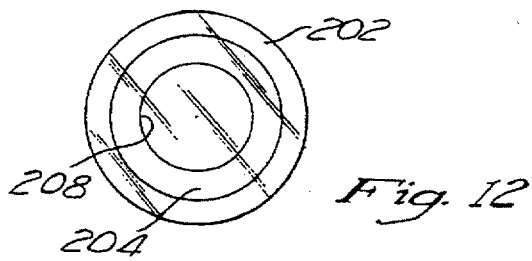

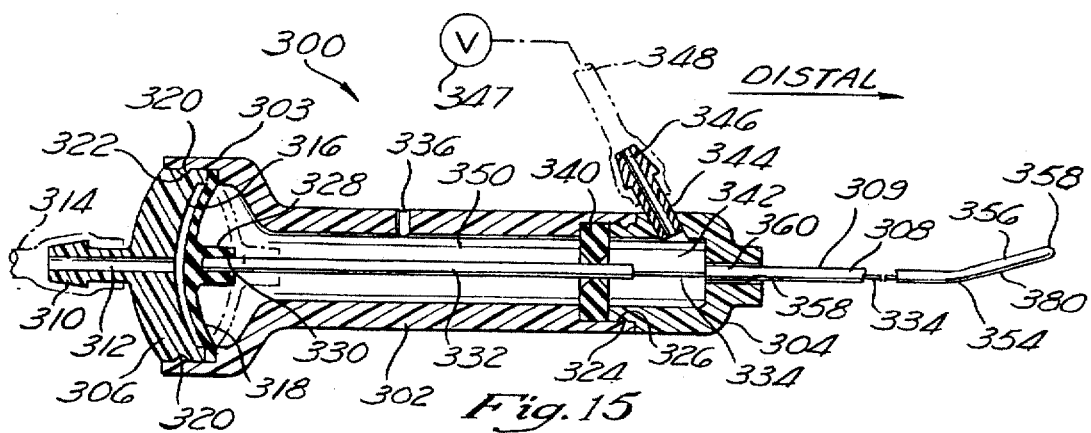
Fig. 15
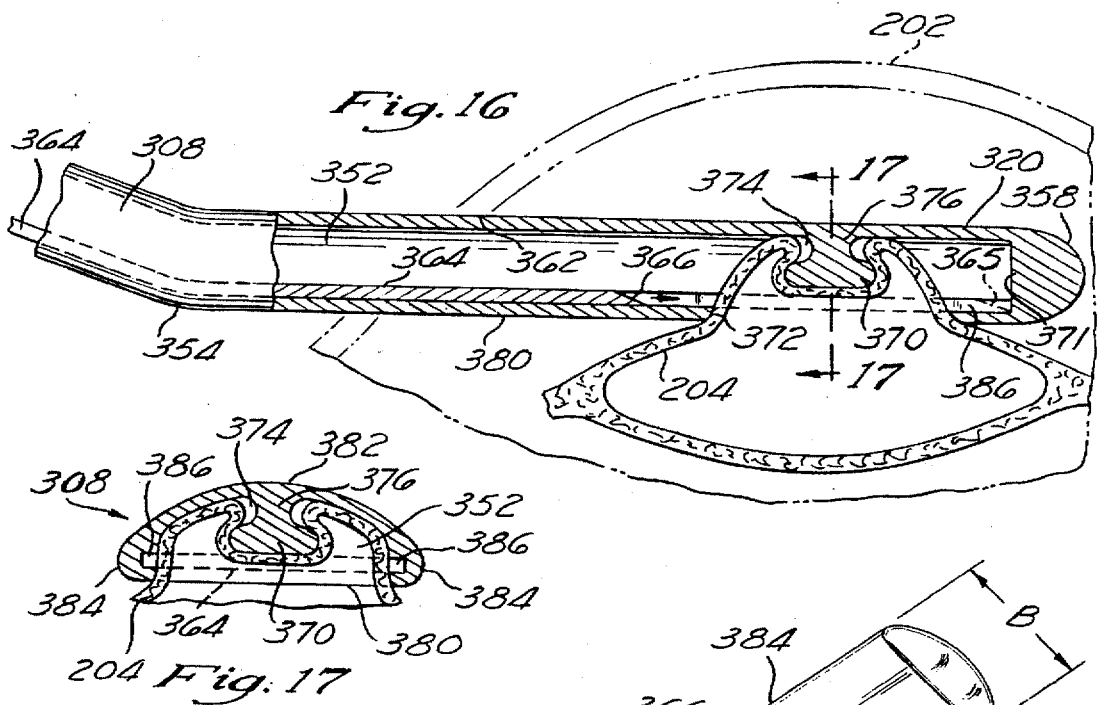
Fig. 16
Fig. 17
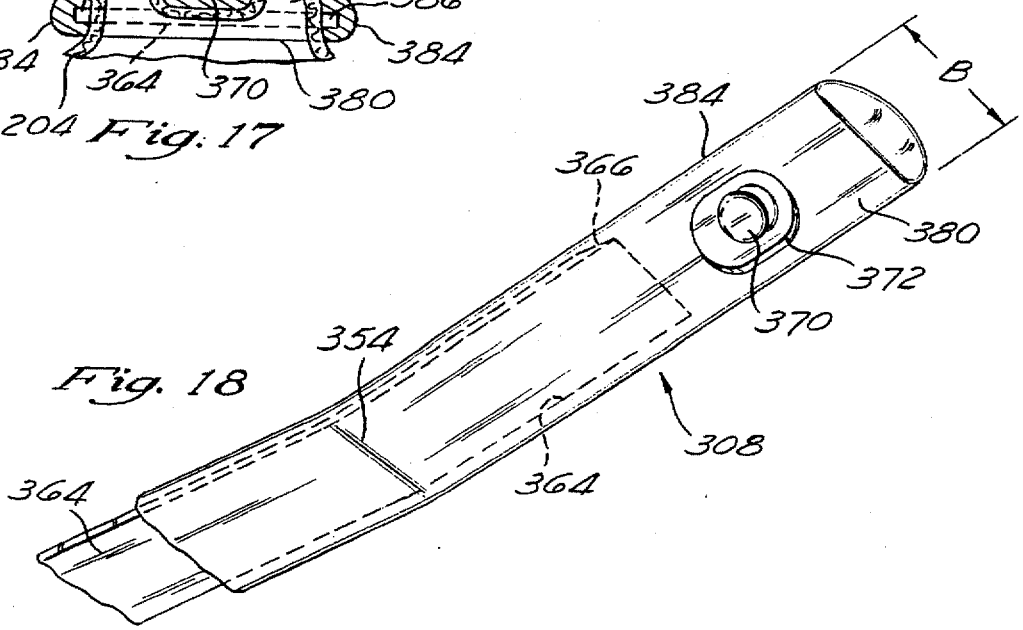
Fig. 18

ANTERIOR CAPSULOTOMY DEVICE AND PROCEDURE

FIELD OF THE INVENTION

The present invention relates generally to medical devices and more particularly to a medical device for performing an anterior capsulotomy procedure wherein the device comprises an elongate probe having a mushroom-shaped form positioned therein about which the capsule folds to provide a desired size and shape of cut.

BACKGROUND OF THE INVENTION

Surgical procedures for replacing the lens of a human eye are well known. To practice such procedures, it is first necessary to form an incision in the patient's cornea or sclera, and subsequently to form an opening in the anterior portion of the capsule which surrounds the patient's lens. The lens is then removed through the opening formed in the capsule and the incision in the cornea and then a replacement lens is substituted therefor.

According to contemporary anterior capsulotomy procedure, the incision in the cornea is made with a scalpel and then a pointed stylet or needle is inserted through the incision in the cornea and is used to rip or tear a generally circular opening in the anterior capsule through which the patient's original lens can be removed and a new lens inserted. More recently, continuous curvilinear capsulorhexis have been performed.

As those skilled in the art will appreciate, the use of such a stylet or needle to tear an opening in the anterior capsule requires a steady hand and a very high degree of skill. Even when practiced by a skilled surgeon, the potential for incorrectly performing the procedure is substantial.

Furthermore, the opening formed in the anterior capsule must be of a diameter slightly less than that of the lens. Although this requires that the opening be stretched somewhat in order to remove the patient's original lens, it allows the anterior capsule to function effectively to maintain the desired or centered position of a new lens. However, forming the opening in the anterior capsule of a larger diameter than that desired or inadvertently tearing the capsule frequently prevents it from properly retaining the new lens.

Further, because of the high degree of skill required to perform an anterior capsulotomy according to contemporary methodology, problems have been known to occur wherein a portion of the lens capsule is cut or torn in an undesirable manner. Contraction of the patient's lens during the procedure further complicates the procedure, thus making problems more likely. Those skilled in the art will appreciate that such cuts or tears may result in severe complications, including infection, potential loss of sight, and damage to the zonules.

As such, although the contemporary anterior capsulotomy procedure has proven generally suitable for lens replacement surgery, it possesses inherent deficiencies which detract substantially from its safety and efficacy. In view of these shortcomings in the prior art, it is highly desirable to provide a means for reliably and safely forming an opening of a desired diameter and shape in the anterior capsule, particularly wherein such means requires less skill to perform than contemporary procedures.

SUMMARY OF THE INVENTION

The present invention specifically addresses and alleviates the above-mentioned deficiencies associated with the prior art. More particularly, the present invention comprises a device for performing an anterior capsulotomy procedure. The device comprises a first tubular member having a wall and also having a lumen formed therethrough. An opening is formed in the wall, preferably proximate a distal end of the tubular member. According to a first preferred embodiment of the invention, the opening has a continuous curvilinear edge which causes a generally circular cut to be made in the capsule as discussed in detail below.

A cutter is movably disposed within the lumen of the first tubular member and a blade is formed upon the cutter. A vacuum port is in fluid communication with the lumen of the first tubular member and is connectable to a vacuum source. As discussed in further detail below, the vacuum port is used to apply a vacuum which draws a portion of the anterior capsule into the first tubular member where it is cut away from the remainder of the anterior capsule by the blade.

An actuator preferably comprises a diaphragm coupled to the cutter and a pressure port in fluid communication with the diaphragm such that applying pressure to the pressure port effects movement, i.e., reciprocation or rotation, of the cutter.

The opening formed in the wall of the first tubular member preferably comprises an opening formed proximate the distal end of the first tubular member. Preferably, the first tubular member further comprises a closed distal tip, which preferably has a smooth or rounded outer surface so as to facilitate easy insertion thereof through the cornea.

The cutter preferably comprises a second tubular member slidably disposed within the first tubular member, wherein the blade is formed at the distal end of the second tubular member. Thus, the blade comprises a sharpened or knife-edge like portion of the second tubular member.

The first tubular member preferably extends from a housing. The second tubular member is preferably slidably disposed partially within the housing and is coupled to the diaphragm such that movement of the diaphragm results in like reciprocal movement of the second tubular member.

Alternatively, the second tubular member is configured so as to effect cutting by rotation, rather than by reciprocation thereof. In this instance, an elongate blade is formed at the distal end of the second tubular member. The elongate blade extends longitudinally for a length approximate that of the length of the opening formed at the distal end of the first tubular member. Rotation of the second tubular member causes the elongate blade to move across the opening in the first tubular member so as to effect cutting.

Those skilled in the art will appreciate that various other configurations of the blade are likewise suitable. For example, the blade may optionally be configured to utilize a combination of reciprocation and rotation such that it moves approximately diagonally across the opening formed in the first tubular member.

The diameter of the second tubular member, proximate the blade thereof, is preferably undercut so as to form a void between the outer wall of the second tubular member and the inner wall of the first tubular member. This forms a flanged knife edge which has been found to be more effective in performing a clean and precise cut in the anterior capsule, as desired.

The diaphragm is disposed within a void formed within the housing such that the diaphragm divides the void into two sections. The pressure port is in communication with one of the two sections such that applying pressure to the diaphragm via the pressure port causes the diaphragm to bow in the distal direction, thereby moving the second tubular member distally.

A spring biases the second tubular member in the proximal direction, thereby assuring positive return of the second tubular member to a ready position when the application of pressure to the pressure port is discontinued.

Alternatively, the blade may be moved both distally and proximally via the application of pressure to the diaphragm, thus providing a pneumatic push-pull configuration. Thus, either of the two sections of the void may be pressurized so as to effect movement of the blade in the desired direction.

When the alternate rotating blade is utilized, rather than the reciprocating blade, pressure may optionally be utilized to effect rotation of the blade in both directions. Otherwise, the blade is preferably rotated so as to effect cutting via the application of pressure and is returned to its original or ready position via a spring.

Those skilled in the art will thus appreciate that any combination of spring biasing and/or pressure may be utilized to effect cutting and return of the cutter to the ready position, as desired.

A vacuum port is preferably formed upon the housing such that the application of vacuum thereto is transmitted through the first tubular member (and preferably the second tubular member as well) to the opening formed in the first tubular member. The vacuum is utilized to draw a portion of the anterior capsule into the first tubular member, as discussed below. The vacuum is optionally also utilized to evacuate the device of the cut portion of the anterior capsule.

The present invention is preferably configured so as to form an opening having a diameter of approximately 3.5–5.5 mm in diameter in the capsule. Optionally, a plurality of devices having different size openings formed in the first tubular member thereof may be provided so as to facilitate the formation of corresponding different size openings in the capsule. The use of such a plurality of devices having different size openings formed therein thus allows a device to be selected based upon the size and geometry of the patient's eyeball and lens. Optionally, the device comprises a plurality of interchangeable first tubular members, each having an opening of a different size formed therein.

The vacuum utilized to facilitate drawing of the capsule into the opening formed in the first tubular member is such that it does not cause harm to the zonules which hold the capsule in place. The continuous curvilinear configuration of the opening in the first tubular member insures that minimal downward pressure of the first tubular member is required for a good seal, thus further minimizing the likelihood of incurring damage to the zonules. Those skilled in the art will appreciate that the specific pressure of the vacuum utilized depends upon various perimeters such the distance of the device from the vacuum source, the size of interconnect tubing utilized, and the specific dimensions of the device itself.

Thus, the method for performing an anterior capsulotomy procedure according to the present invention comprises the steps of: forming an incision in a patient's cornea; inserting the first tubular member through the incision; positioning the continuous curvilinear opening in the first tubular member centrally with respect to the capsule and in light contact with the capsule so as to form a seal therewith; applying a vacuum to the first tubular member so as to cause a portion of the capsule to be drawn into the first tubular member through the opening therein; and actuating the cutter so as to cause the cutter to cut that portion of the capsule disposed within the first tubular member away from the remaining portion of the capsule.

The probe is positioned over the center of the lens with the iris retracted. The iris is dilated or retracted with drugs so as to provide access to the anterior capsule. The opening in the first tubular member is preferably aligned with the lens such that the first tubular member is approximately tangent to the outer surface of the lens.

The application of vacuum pulls the anterior capsule through the opening formed in the first tubular member, stretching the membrane as it passes through the opening. The hole cut in the anterior capsule has an increased surface area due to this stretching of the membrane and the tension in the membrane which results therefrom.

During performance of the procedure of the present invention, the first tubular member is pushed down lightly so as to establish adequate seal between the perimeter of the continuous curvilinear opening in the first tubular member and the surface of the anterior capsule, thereby insuring that the vacuum formed in the first tubular member draws a portion of the anterior capsule into the first tubular member. The application of such light pressure mitigates the likelihood of causing damage to the zonules, as discussed above.

Rather than maintaining downward pressure with the first tubular member against the anterior capsule, the first tubular member is preferably either allowed to remain in position with minimal or no downward pressure or, alternatively is lifted slightly. By eliminating the need for substantial downward pressure, the probability of causing damage to the zonules is minimized.

The hole cut in the anterior capsule is generally circular in shape due to the continuous curvilinear configuration of the edge of the opening in the first tubular member through which the surface of the anterior capsule is drawn. The continuous curvilinear configuration of the edge of the opening in the first tubular member thus provides a smooth, generally circular opening in the anterior capsule which substantially lacks undesirable rough edges, sharp bends, or generally ragged features.

The step of actuating the cutter preferably comprises applying pressure to the diaphragm so as to effect movement of the cutter. The pressure applied to the diaphragm preferably causes the diaphragm to bow distally so as to cause the second tubular member to move distally, thereby causing the blade formed thereon to travel across the opening formed in the first tubular member such that that portion of the anterior capsule which has been drawn into the opening in the first tubular member is cut away from the remaining portion of the anterior capsule.

The incision formed in the cornea is preferably approximately 2.5–3.5 mm in length so as to facilitate insertion of the first tubular member therethrough and is preferably stepped or staggered so as to eliminate the need for sutures at the completion of the surgical procedure.

Thus, the anterior capsulotomy device of the present invention provides a clean and accurate cut so as to form an opening of a desired size and configuration in the anterior capsule. Performance of the procedure according to the present invention is not substantially dependent upon the skill of the surgeon, as in contemporary methodology.

It is important to note that the membrane of the anterior capsule stretches substantially due to the vacuum applied at the continuous curvilinear opening formed in the first tubular member, as mentioned above. Thus, although the first tube preferably has an outer diameter of between 0.75 mm and 2 mm, preferably approximately 1.75 mm, a 3.5–5 mm hole results from cutting the stretched portion of the anterior capsule.

In an alternative embodiment of the device for performing an anterior capsulotomy procedure according to the present invention, the device comprises an elongate tubular member or probe extending from the body of the device and having proximal and distal ends. The tubular member comprises a wall and a lumen formed generally therethrough. An opening is formed in the wall proximate the distal end of the tubular member. A cutter is movably disposed within the lumen of the tubular member. The cutter has a blade formed thereon.

A vacuum port is in fluid communication with the lumen of the tubular member to facilitate the application of a vacuum thereto, so as to draw a portion of an anterior capsule into the tubular member. An actuator effects movement of the cutter so as to move the blade across the opening formed in the wall of the tubular member and thereby cut that portion of the anterior capsule drawn into the tubular member.

The opening is configured to draw in a portion of an anterior capsule when a vacuum is applied to the vacuum port in a manner which causes the cutter to form a generally circular cut of a predetermined size in the anterior capsule when the actuator is actuated.

The tubular member comprises a generally flat lower surface and a bowed upper surface so as to substantially reduce the cross-sectional area thereof, and also so as to provide an enhanced vacuum seal with the capsule about the opening of the tubular member during use thereof. Reducing the cross-sectional area of the tubular member similarly reduces the size of the opening that must be formed in the cornea to facilitate insertion of the tubular member therethrough. Thus, trauma to the cornea is reduced and faster healing is facilitated.

The actuator preferably comprises a diaphragm in mechanical communication with the cutter and a pressure port in fluid communication with the diaphragm such that applying pressure to the pressure port effects movement of the cutter. The actuator preferably further comprises a wire interconnecting the diaphragm and the cutter. The wire is configured to slide or translate within the tube so as to effect movement of the cutter in response to the application of pressure to the diaphragm.

The actuator preferably comprises a rigid, hollow tube attached at a proximal end thereof to the diaphragm and attached at a distal end thereof to the wire.

A bend is preferably formed in the tubular member to facilitate manipulation thereof. The use of such a bend makes manipulation of the distal end of the probe or tubular member easier by providing a more natural handhold position for the user and also by making it easier to place the lower surface of the tubular member in laminar juxtaposition to the upper surface of the capsule, thereby insuring a better vacuum seal.

Thus, two different mechanisms are utilized according to the present invention to assure an adequate vacuum seal between the opening formed in the distal end of the tubular member and the anterior capsule. First, the lower surface of the tubular member is formed so as to be generally flat, such that improved contact between the tubular member and the upper surface of the capsule is achieved. Second, the tubular member is bent at an angle which provides more natural manipulation and holding thereof, such that the distal end of a tubular member may more easily be placed at the desired orientation with respect to the anterior capsule and maintained in that desired orientation for the duration of the procedure.

The bend is preferably formed at an angle of between approximately 10 degrees and approximately 20 degrees, preferably approximately 15 degrees.

According to this preferred configuration of the present invention, a form is disposed within the tubular member proximate the opening thereof. A portion of the anterior capsule folds about the form after being drawn into the tubular member, in a manner which substantially increases the quantity of the capsule drawn into the tubular member, and thus likewise increases the size of the opening cut into the anterior capsule by the cutter. Thus, a form facilitates the cutting of a larger opening in the anterior capsule for a given diameter or cross-sectional area of the tubular member. Use of the form allows a larger opening to be formed in the anterior capsule than could be accomplished without the form. The desirable benefit of this is that the cross-sectional diameter of the tubular member is minimized for a given size of opening to be formed in the anterior capsule via the use of such a form.

The form is preferably generally shaped so as to resemble a mushroom. That is, the form generally comprises an enlarged head portion and a shaft of reduced diameter. The shaft or portion of reduced diameter has the additional benefit of causing the formation of a void about the form which transmits vacuum in a desirable manner so as to assure that a sufficient quantity of the anterior capsule is drawn into the tubular member and maintained in position for cutting prior to actuation of the cutter.

The cutter is constrained to move longitudinally across the opening via a guide preferably comprised of two tracks formed within and extending along at least a portion of the tubular member within which the cutter slides.

The cutter preferably comprises an upward bend formed therein proximate the blade thereof and a downward bend formed therein intermediate the upward bend and the blade. The upward bend and the downward bend cooperate to bias the blade downward so as to enhance the cutting of a capsule therewith.

Thus, according to the methodology of the present invention, a clean, precisely located opening is formed safely and reliably in the anterior capsule without tearing and without the need for a high degree of skill. The probability of inadvertently tearing or puncturing membranes within the eye is substantially reduced. Further, the size of the required opening in the cornea is minimized so as to reduce trauma.

These, as well as other advantages of the present invention will be more apparent from the following description and drawings. It is understood that changes in the specific structure shown and described may be made within the scope of the claims without describing from the spirit of the invention.

BRIEF DESCRIPTION OF THE DRAWINGS

FIG. 1 is a prospective view of a human eyeball illustrating the practice of an anterior capsulotomy procedure according to the methodology of the prior art;

FIG. 2 is a prospective view of the a bent stylet or needle as used to tear an opening in the anterior capsule according to the anterior capsulotomy methodology of the prior art;

FIG. 3 is a cross-sectional side view further illustrating the anterior capsulotomy methodology according to the prior art;

FIG. 4 is a front plan view of the patient's cornea showing the ragged opening formed therein with the bent stylet or needle according to the anterior capsulotomy methodology of the prior art;

FIG. 5 is a cross-sectional side view of the anterior capsulotomy device of the present invention;

FIG. 5a is a perspective view of the anterior capsulotomy device of FIG. 5;

FIG. 5b is an exploded perspective view of the anterior capsulotomy device of FIG. 5a;

FIG. 6 is an enlarged side view of the distal end of the first tubular member of FIG. 5, rotated 90 degrees about the horizontal axis;

FIG. 7 is an enlarged cross-sectional side view of the distal end of the first tubular member of FIG. 5, showing the blade formed upon the second tubular member thereof;

FIG. 8 is a perspective view of an eyeball having the device for performing an anterior capsulotomy procedure according to the present invention inserted through an incision formed in the cornea and positioned above the anterior capsule so as to form an opening at the desired location in the anterior capsule in order to facilitate removal and replacement of the patient's lens;

FIG. 9 is a cross-sectional side view of the eye and the device for performing an anterior capsulotomy procedure according to the present invention taken along lines 9 of FIG. 8;

FIG. 10 is an enlarged cross-sectional side view of the eye and device of FIG. 9 showing the portion of the anterior lens to be cut from the remaining anterior lens drawn into the opening formed proximate the distal end of the first tubular member and also showing the cutter positioned such that further distal movement thereof will effect cutting of that portion of the anterior lens contained within the first tubular member;

FIG. 11 is an end view of the device for performing an anterior capsulotomy of FIG. 10, similarly showing a portion of the anterior lens drawn into the first tubular member;

FIG. 12 is a front plan view of the patient's cornea showing the smooth opening formed therein with the anterior capsulotomy device of the present invention;

FIG. 15 is a cross-sectional side view of an alternative configuration of the anterior capsulotomy device of the present invention;

FIG. 16 is an enlarged side view of the distal tip of the probe of the anterior capsulotomy device of FIG. 15, partially in cross section;

FIG. 17 is a cross-sectional end view of the probe of FIG. 16 taken along lines 17 thereof;

FIG. 18 is a perspective view of the distal end of the probe of FIG. 15;

DETAILED DESCRIPTION OF THE PREFERRED EMBODIMENT

Figure 13:
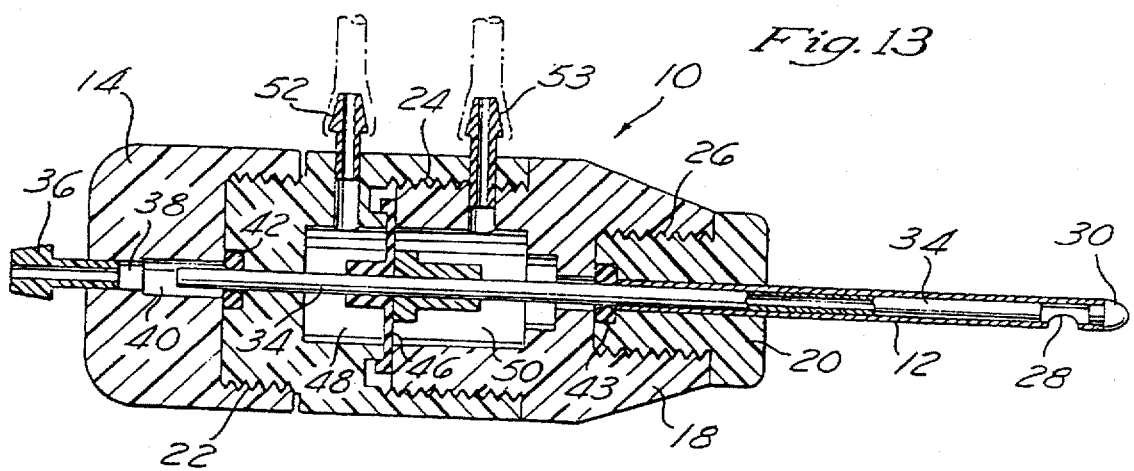
FIG. 13 is a cross-sectional side view of an alternative configuration of the present invention wherein a second pressure port replaces the spring thereof so as to effect return of the cutter to a ready position.

The detailed description set forth below in connection with the appended drawings is intended as a description of the presently preferred embodiments of the invention, and is not intended to represent the only form in which the present invention may be constructed or utilized. The description sets forth the functions and sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The anterior capsulotomy device of the present invention is illustrated in FIGS. 5–11 and 13–20 of the drawings which depict a presently preferred embodiments of the invention. FIGS. 1–4 depict prior art methodology and FIG. 12 depicts the opening formed in the anterior capsule according to the methodology of the present invention.

Referring now to FIGS. 1–4, to perform a contemporary anterior capsulotomy procedure upon a patient's eye 110, an incision 112 is formed in the cornea 114 to provide access to the anterior capsule 122. A stylet or needle 116 having a bend 118 formed therein such that the tip 120 thereof may readily be used to tear the anterior capsule 122 is inserted through the incision 112 formed in the cornea 114. Forceps may be utilized to effect a continuous curved capsulotomy. The bent tip 120 of the needle 116 is then used to puncture and tear the anterior capsule 122 so as to form an opening of the desired size and configuration therein in order to facilitate removal of the patient's original lens 124 and replacement thereof with a new lens. This procedure involves repeatedly puncturing the anterior capsule 122 with the sharp tip 120 of the stylet or needle 116 and pulling on the stylet or needle 116 so as to make a small tear in the anterior capsule 122. Such repeated tearing of the anterior capsule 122 forms an opening 126 in the anterior capsule 122 through which replacement of the lens 124 may be effected.

Performing an anterior capsulotomy procedure according to contemporary methodology requires that the surgeon possess substantial skill. Mistakes occurring during the procedure may result in damage to the anterior capsule which prevents its later function of supporting the new lens. Improperly forming the opening 126 in the anterior capsule 122 or otherwise undesirably tearing the anterior capsule 126 may thus result in inability of the remaining portion of the anterior capsule 122 to maintain the replacement lens in a centered or desired position.

With particular reference to FIG. 4 the resultant opening 126 formed in the anterior capsule 122 is comparatively ragged, thereby emphasizing the crude nature of the contemporary anterior capsulotomy procedure. As will be appreciated, the repeated puncturing and tearing of the anterior capsule is a tedious and time consuming procedure which is difficult to perform and which may potentially result in permanent damage to the eye.

Referring now to FIGS. 5–7, the anterior capsulotomy device of the present invention generally comprises a housing 10 having a first elongate tubular member 12 extending from the distal end thereof. The first tubular member 12 preferably has an outer diameter of between 0.75 mm and 2 mm, preferably approximately 1.75 mm.

The housing 10 preferably comprises a proximal section 14, a mid section 16, a distal section 18, and a cap 20. The proximal section 14 preferably engages the mid section 16 via threaded coupling 22. Similarly, the mid section 16 preferably engages the distal section 18 via threaded coupling 24 and the distal section 18 preferably engages the cap 20 via threaded coupling 26.

An opening 28 is formed proximate the distal end 30 of the first tubular member 12. The opening 28 provides passage through the wall of the first tubular member 12 into the lumen thereof. A smooth or rounded tip 32 terminates the first tubular member 12. A second tubular member 34 is disposed partially within the first tubular member 12 and partially within the housing 10. Like the first tubular member 12, a lumen is formed within the second tubular member 34.

The opening 28 comprises a continuous curvilinear edge which facilitates the formation of a generally circular opening in the anterior capsule lacking jagged edges or abrupt bends.

A vacuum port 36 facilitates the application of a vacuum to the lumens of the first 12 and second 34 tubular members such that the vacuum is provided at the opening 28 formed proximate the distal end of the first tubular member 12. Vacuum applied to the vacuum port 36 is transmitted to the second tubular member 34 via first 38 and second 40 bores formed in the proximal section 14 of the housing 10 and then is transmitted through the lumen of the second tubular member 34 to the lumen of the first tubular member 12 at the opening 28 formed therein. First o-ring seal 42 prevents leakage of the vacuum along the outer surface of the second tubular member 34 within the mid section 16 of the housing 10.

A void 44 is formed within the housing 10 preferably by cooperation of the mid 16 and distal 18 sections thereof. A flexible diaphragm 46 separates the void into first 48 and second 50 sections thereof. The diaphragm 46 is preferably comprised of a resilient polymer material. However, those skilled in the art will recognize that a variety of other materials are likewise suitable for use as the diaphragm 46.

A pressure port 52 facilitates the transmission of air pressure into the first section 48 of the void 44. A collar 54 rigidly attached to the second tubular member 34 facilitates coupling of the diaphragm 46 to the second tubular member 34 such that distal movement of the diaphragm 46 results in like distal movement of the second tubular member 34. The diaphragm 46 attaches to the second tubular member 34 in a substantially airtight manner so as to mitigate the leakage of air therebetween. The periphery of the diaphragm 46 is captured intermediate mid the section 16 and the distal section 18 of the housing 10 so as to provide a substantially airtight seal between the first 46 and second 50 sections of the void 44.

Spring 60 biases the second tubular member 34 proximally such that when pressure is not applied at the pressure port 52, the second tubular member 34 is maintained in a proximal position thereof. The application of pressure to the pressure port 52 causes the diaphragm 46 to flex or bow distally so as to push against the collar 54 and thereby cause the second tubular member 34 to move to a distal position thereof against the urging of spring 60.

Second o-ring seal 43 provides a substantially airtight seal between the distal section 18 of the housing 10 and the cap 20 thereof so as to substantially mitigate air leakage from the second section 50 of the void 44.

With particular reference to FIGS. 6 and 7, the second tubular member 34 has a blade 64 formed at the distal end thereof. The blade 64 is formed so as to comprise an undercut 66 which forms a void 68 intermediate the outer surface of the second tubular member 34 and the inner surface of the first tubular member 12. It is thought that such an undercut provides cleaner and more thorough cutting of the anterior capsule.

With particular reference to FIG. 7, the blade further comprises a bevel 70 formed such that the tip 72 of the blade 64 is positioned away from the inner wall of the first tubular member 12, preferably by approximately 0.001 inch (dimension A). Thus, both the undercut 66 and the bevel 70 are easily machined on the distal end of the second tubular member 34. Those skilled in the art will appreciate that various other configurations of the blade are likewise suitable. Indeed, the blade need not comprise a portion of a tubular member, but rather may comprise various other structures which are suitable for cutting a portion of the lens which extends through the opening 28 of the first tubular member 12.

Referring now to FIGS. 8–12, the methodology of performing an anterior capsulotomy according to the present invention is illustrated. With particular reference to FIGS. 8 and 9, an incision 200 is formed in the cornea 202 and the first tubular member 12 is inserted therethrough. As best shown in FIG. 9, the opening 28 of the first tubular member 12 is positioned centrally over the anterior capsule 204 where it is desired to form an opening therein. The first tubular member 12 is preferably positioned such that it is approximately tangent to the anterior capsule 204 and is pressed lightly thereagainst so as to form a seal, such that when vacuum is applied to the vacuum port 36 a portion of the anterior capsule is drawn into the opening 28.

The continuous curvilinear edge of the opening 28 facilitates the formation of a vacuum seal between the first tubular member 12 and the anterior capsule 204 so as to assure that the anterior capsule 204 is properly drawn into the first tubular member 12.

With particular reference to FIGS. 10 and 11, vacuum is applied to the vacuum port 36 so as to cause a portion 206 of the anterior capsule 204 to be drawn into the opening 28 formed in the first tubular member 12. Once the portion 206 of the anterior capsule 204 is drawn into the opening 28, pressure is applied to the pressure port 52, thus causing the diaphragm 46 to bow distally so as to urge the second tubular member 34 distally, against the urging of spring 60 such that the blade 64 thereof moves across the opening 28 so as to cut the portion 206 of the anterior capsule 204 away from the remainder thereof.

Optionally, the present invention is configured such that the application of vacuum to vacuum port 36 causes the evacuation of the lumen formed in the first elongate member so as to effect removal of the cut portion of the anterior capsule therefrom. As those skilled in the art will appreciate, the cut portion of the anterior capsule may then be captured in a trap or filter disposed intermediate the anterior capsulotomy device and the vacuum source.

With particular reference to FIG. 12, it is important to note that application of the vacuum causes the anterior capsule 204 to stretch substantially such that the 1.75 mm outer diameter of the first tubular member 12 makes an opening 208 in the anterior capsule 204 having a diameter of approximately 3.5–4.5 mm. Thus, the anterior capsule is cut while under tension such that after cutting, when tension is released, the opening 208 formed in the anterior capsule 204 is substantially larger than the opening 28 formed in the first tubular member 12, and it is also substantially larger than the outer diameter of the first tubular member 12 itself.

Referring now to FIG. 13, an alternative configuration of the present invention is illustrated. In this alternative configuration of the present invention, a second pressure port 53 replaces the spring 60 so as to facilitate positive return of the second tubular member 34 to the pre-use or ready position thereof. Thus, after pressure is applied to the diaphragm 46 via the first pressure port 52 so as to cause the second tubular member 34 to extend so as to effect cutting of the anterior capsule, pressure is applied to the second pressure port 53 so as to cause the second tubular member 34 to retract.

Figure 14:
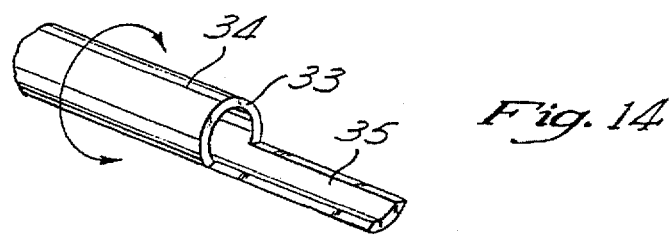
FIG. 14 is a perspective view of an alternative configuration of the cutter, the alternative configuration being configured to rotate rather than reciprocate.

Referring now to FIG. 14, an alternative configuration of the cutter or second tubular member 34 comprises a blade 35 extending from the distal end 33 thereof. In this alternative configuration, the second tubular member 34 is configured so as to rotate, rather than reciprocate. Thus, the blade 35 sweeps across the opening 28 formed at the distal end of the first tubular member 12 so as to facilitate cutting of the anterior capsule.

Referring now to FIGS. 15 and 16, an alternative configuration of the present invention is illustrated. In this alternative configuration of the present invention, the anterior capsulotomy device 300 comprises a body 302 to which a distal end member 304 and a proximal end member 306 are attached. An elongate probe 308 extends from the distal end member 304. A pressure fitting 310 is formed upon the proximal end member 306 and comprises a bore 312 which is formed continuously through the pressure fitting 310 and the proximal end member 306 so as to facilitate the application of pressure from pressure tubing 314 to pressure chamber 316.

The pressure chamber 316 is defined within the body 302 by the proximal end member 306 and a flexible diaphragm 318 which is configured to move in response to the application of pressure via pressure tubing 314. A region of increased diameter 303 formed at the proximal end of the body 302 defines the pressure chamber 316 so as to provide sufficient surface area for the diaphragm 318 to be acted upon in a desired manner by pressure provided via pressure tubing 314. As those skilled in the art will appreciate, the force applied to the diaphragm 318 is proportional to the surface area upon which such pressure acts. Vent 336 formed in the body 302 allows air to be vented from the body 302 when the diaphragm 318 is actuated via pressure from the pressure tubing 314.

The diaphragm 318 is preferably configured such that an over-center device is defined thereby. Thus, the diaphragm is stable in either the unactuated or actuated position and moves quickly from the unactuated to the actuated position due to the over-center configuration thereof. Such over-center configuration of the diaphragm is achieved by configuring the diaphragm 318 such that the diameter of the outer periphery thereof is substantially less than the length of an arc defined by the curved surface of the diaphragm intermediate two diametrically opposed points on the periphery thereof. That is, the diaphragm is caused to bow in either the unactuated or actuated position such that it becomes compressed as it begins to travel from the unactuated to the actuated position, and then stretches and becomes uncompressed as it completes such travel, thereby increasing the speed of the cutter as the diaphragm stretches and approaches the actuated position thereof.

The proximal end member 306 is preferably attached to the body 302 via a snap or detent fit. As those skilled in the art will appreciate, adhesive bonding, thermal bonding, ultrasonic bonding, etc. may be used in place of such detent or in combination therewith. The distal end member 304 is similarly attached to the distal end of the body 302 via an annularly configured female detent 324 formed in the distal end 304 and a complimentary annularly configured male detent 326 formed in the body 302.

The diaphragm 318 comprises preferably a boss 328 having a bore 330 formed therein. The bore 330 of the diaphragm 318 receives the proximal end of force transmitting hollow tube 332. The force transmitting tube 332 is preferably formed of a hollow metal or durable plastic, so as to minimize the inertia associated therewith and thereby maximize the acceleration and velocity thereof when moved by the diaphragm 318 during the cutting process, as described in detail below. Wire 334 is rigidly attached at the proximal end thereof to the distal end of the tube 332 such that lateral displacement or sliding movement of the tube 332 due to actuation of the diaphragm 318 effects similar movement of the wire 334. The wire 334 extends through the probe 308.

Alternatively, the tube 332 could act directly upon a blade without an interconnecting wire. This configuration may particularly be utilized absent the bend 354 formed in the probe 308.

O-ring or seal 340 facilitates lateral displacement of the tube 332 therethrough while mitigating vacuum loss between the seal 340 and the tube 332. Vacuum is applied to vacuum chamber 342 via vacuum fitting 344 having a bore 346 formed therein and configured for attachment to vacuum source 347 through vacuum tubing 348. Vacuum applied to the vacuum chamber 342 is thereby substantially prevented from leaking into the central portion 350 of the body 302 and then out via vent 336. The vacuum is applied to opening 372 through bore 352 (best shown in FIG. 16) formed in the interior of probe 308.

The tip 358 is preferably rounded so as to reduce the likelihood of trauma during use. A bend 354 is preferably formed in the elongate probe 308 so as to more desirably position the distal end thereof during use. The bend 354 preferably comprises a bend of between approximately 10 and 20 degrees, preferably approximately 15 degrees. Such a bend has been found to be optimal in facilitating easy manipulation of the device and also in providing a reliable vacuum seal to the anterior capsule.

The proximal end 306 of the probe is securely attached to the distal end member 304 and is positioned within bore 358 formed therein such that an airtight fitting between the distal end member 304 and the probe 308 is formed.

The probe or elongate tubular member 308 is preferably between approximately 0.80 and approximately 1½ inches in length. Those skilled in the art will appreciate that the elongate member 308 may be formed to have any desired length.

Figure 20:
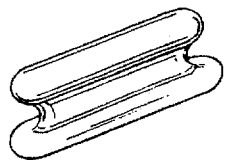
FIG. 20 is a perspective view of an alternative configuration of the form of FIGS. 16–18.

A generally mushroom-shaped form 370 extends inwardly from the upper wall 320 of the probe 308 and defines an annular void 374 about the stem 376 thereof during use so as to maintain the application of vacuum to the capsule 204, as discussed in detail below. As shown in FIGS. 16 and 18, the form 370 is generally circular in configuration. Alternatively, the form is elongated in the longitudinal direction of the probe 308 as shown in FIG. 20, such that it extends substantially the length of the opening 372 and slightly beyond, if desired.

Since this alternative configuration of the present invention is generally intended to be disposable, i.e., configured for a single use only, a return spring for causing the cutter 364 to withdraw or move proximally is not required. Similarly, no pressure port for pressurizing the interior of the body 350 so as to effect withdrawal of the cutter 364 is provided. However, as those skilled in the art will appreciate, either a return spring or pressure port for pressurizing the body 350 may be provided in order to effect withdrawal of the cutter 364, as desired.

Referring now to FIGS. 17 and 18, the probe 308 has a generally flattened or D-shaped cross section with the flat portion of the D being the lowermost or capsule-contacting portion of the probe. Such configuration of the probe 308 substantially reduces the cross-sectional area thereof, thereby facilitating entry of the probe through the cornea 202 via an opening 362 formed in the cornea 202 having minimal size. As those skilled in the art will appreciate, it is desirable to form the opening 362 in the cornea 202 so as to be as small as possible in order to facilitate more rapid healing thereof. The width, dimension B, of the probe 308 is preferably between approximately 0.08 and 0.12 inch, preferably approximately 0.10 inch. Use of this alternative configuration of the present invention facilitates the performance of an anterior capsulotomy procedure requiring an opening in the cornea approximately equal to the width B of the probe 308, thus minimizing trauma to the cornea and facilitating rapid healing thereof.

Furthermore, by forming the probe 308 to have a substantially flat lower surface 380, better contact with the capsule 204 is attained, thereby assuring a sufficient seal between the probe 308 and the anterior capsule 204 so as to facilitate drawing of a portion of the capsule 204 into the probe 308. The bend 354 formed in the probe 308 also causes the distal end of the probe 308 to be more easily positioned upon the capsule 204 with the lower surface 380 of the probe 308 flush with the capsule 204, so as to assure an adequate vacuum seal therewith about the opening 372.

As shown in FIG. 17, the upper surface 382 of the probe 308 is generally convex. The sides 384 are rounded so as to provide a smooth transition between the lower surface and the upper surface 382.

A guide comprising tracks 386 formed upon either side of the interior of the probe 308 receives the generally flat cutter 364, so as to assure desired movement of the cutter 364 across the opening 372, through which a portion of the capsule 204 is drawn via the vacuum.

Figure 19:
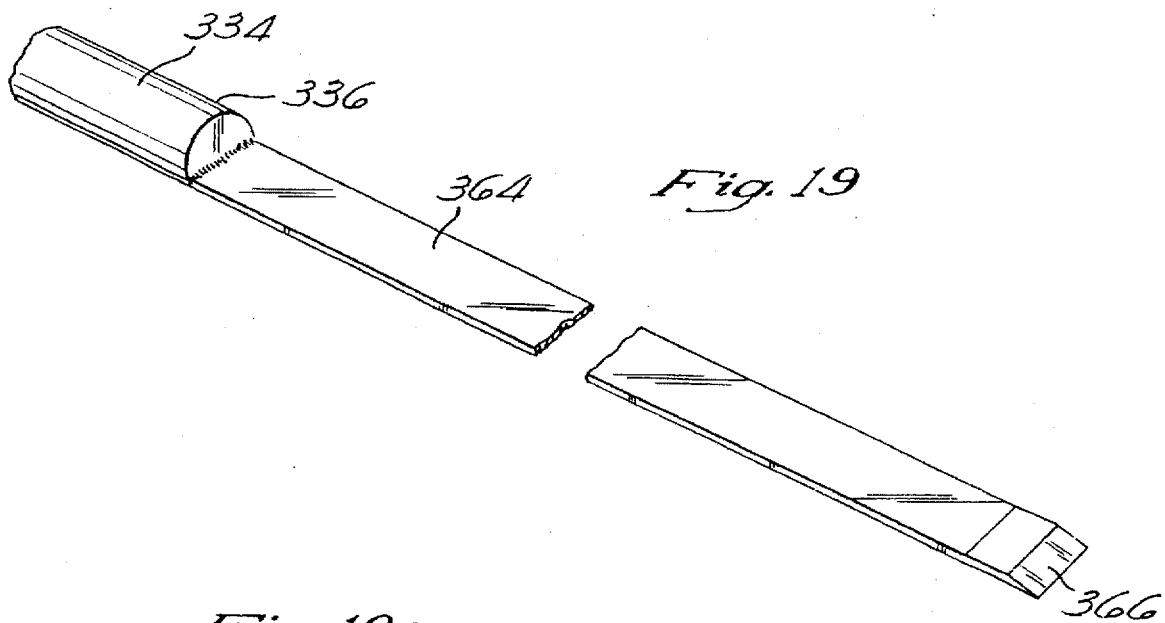
FIG. 19 is a perspective view of the cutter, showing its attachment to the wire for effecting movement thereof.

Referring now to FIG. 19, a cutter 364 is formed to the distal end 365 of the wire 334, preferably via welding, brazing, soldering, etc., and has a blade 366 formed at the distal end thereof such that the cutter 364 is configured to perform a cutting movement across opening 372 formed proximate the tip 358 of the probe 308 when pressure is applied to the pressure chamber 316. The opening 372 is preferably generally elliptical or oblong in configuration, having a longitudinal or long diameter of approximately 0.10 inch and having a transverse or short diameter of approximately 0.08 inch. This will result in an opening having a diameter of approximately 5 mm being formed in the anterior capsule. The opening 372 is preferably configured such that it is spaced away from the distal end of the probe 308 by a distance of approximately 0.05 inch. The cutter 364 is generally flat, such that it extends across the width of the interior 352 of the probe in the area proximate the opening 372 thereof. The cutter is preferably between approximately 0.003 and approximately 0.007 inch thick to provide the desired degree of flexibility.

Figure 19A:
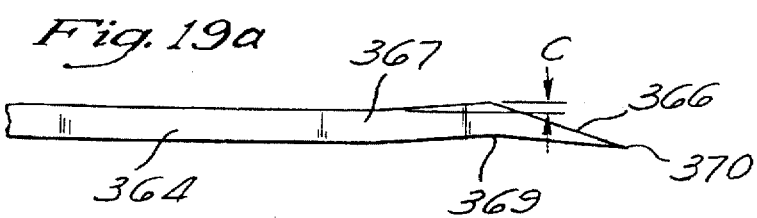
FIG. 19a is an enlarged side view of the cutter showing the blade thereof.

Referring now to FIG. 19a, the distal end of the cutter 364 is preferably configured so as to have an upward bend 367 formed therein and also to have a downward bend 369 formed distal of the upward bend 367, in a manner which causes the tip 370 to be urged downwardly, into a desired position along the opening 372, so as to insure proper cutting of the capsule 204. The tip 370 of the blade 366 is thereby biased downwardly during the cutting process. Thus, the two bends 367 and 369 formed in the cutter 364 assure that the cutting edge or tip 370 of the cutter travels along a desired path so as to achieve optimal cutting therewith.

The two bends 367 and 369 are configured such that the cutter 364 bows upward a distance of between approximately 0.003 and approximately 0.006 inch at the highest point thereof, dimension C.

Figure 19B:
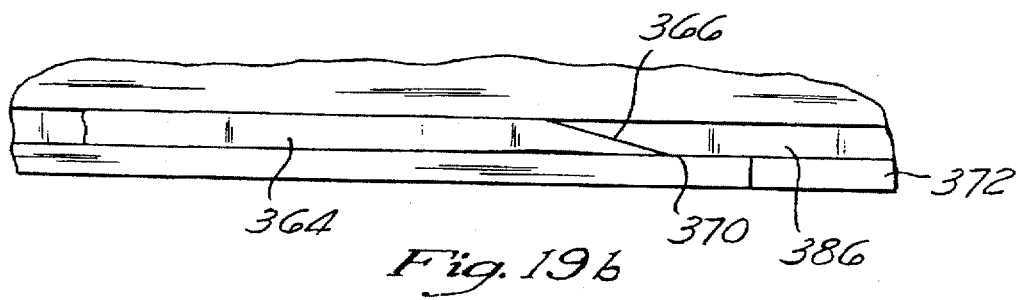
FIG. 19b is an fragmentary side view of the cutter and probe showing one of the tracks within which the cutter moves.

Referring now to FIG. 19b, the cutter 364 is shown disposed within one of the guide tracks 386 where it is positioned just proximal of the opening 372 formed in the probe 308, as it is just prior to being actuated.

In use, a small opening 362 (FIG. 16) is formed in the cornea 202 so as to receive the probe 308. Because of the use of the probe 308 configured according to the present invention, the size of the opening 362 formed in the cornea 202 is minimized. The bend 354 formed in the probe 308 facilitates easy manipulation of the distal end thereof to a position wherein the opening 372 formed in the probe 308 is immediately above the desired portion of the capsule 204 to be cut. The bend 354 formed in the probe 308 also allows the distal end of the probe 308 to easily be manipulated to a position wherein the flat surface 380 thereof lies flush against the upper surface of the lens capsule 204, so as to achieve a desired vacuum seal between the lens capsule 204 and the lower surface 380 of the probe 308. The substantially flat construction of the lower surface 380 of the probe 308 facilitates the formation of such vacuum seal about the opening 372 thereof.

Vacuum is applied to the vacuum chamber 342 via vacuum source 347 and is transmitted through the length of the probe 308, along the interior 352 thereof, such that a portion of the capsule 204 is drawn into the interior 352 of the probe 308 by the vacuum.

As shown in FIGS. 16 and 17, that portion of the capsule 204 drawn into the interior 352 of the probe 308 tends to wrap around the mushroom-shaped form 370 in a manner which increases the amount of the capsule 204 drawn into the probe 308 through opening 372. The capsule tends to fold in a manner which allows more of the capsule to be contained within the probe 308. Such folding of the capsule 204 also causes the capsule to be drawn more uniformly into the opening 372, such that a more nearly circular opening is formed in the capsule 204. The use of such a form allows a larger opening to be cut in the capsule 204 with a given size probe 308. Likewise, this allows the cross-sectional area of the probe 308 to be reduced substantially for a given desired size of cut to be formed in the capsule 204. The present invention minimizes the size of the opening 362 which must be formed in the cornea 202 in order to effect an anterior capsulotomy procedure. More importantly, the present invention minimizes the size of the opening which must be formed in the cornea 202 for a given size of opening to be formed in the anterior capsule.

The void 374 formed about the stem 376 of the mushroom-shaped form 370 allows vacuum to be readily transmitted about the stem 376, so as to assure that a desired portion of the capsule 204 is pulled into the probe 308 and maintained in place prior to actuation of the cutter 364.

After the desired portion of the capsule 204 has been drawn into the probe 308, pressure is applied to the pressure chamber 316 via pressure tubing 314, so as to cause the diaphragm 318 to be urged quickly in a distal direction, thereby driving the tube 332 distally. Since the wire 334 is rigidly connected to the tube 332, the wire 334 is similarly driven distally along the length of the probe 308. The wire 334 possesses sufficient rigidity so as not to buckle substantially during the actuation process. The wire also possesses sufficient flexibility so as to accommodate the bend 354 formed in the probe 308. As those skilled in the art will appreciate, various metal and polymer materials are suitable for such use.

The cutter 364, which is formed to the distal end of the wire 334 thus moves distally, guided by tracks 386. Distal movement of the cutter 364 causes the blade 366 thereof to cut that portion of the capsule 204 drawn into the probe 308 away from the remainder of the capsule 204, thus forming a desired opening in the capsule 204. The cutter 364 preferably continues to move distally until the blade 366 thereof contacts end member or stop 371 formed at the distal end of the probe 308, thereby insuring complete and effective cutting of the anterior capsule 204.

Preferably, the entire device 300, including the housing and probe 308 thereof are formed so as to be disposable.

It is understood that the exemplary anterior capsulotomy devices and methodology for using the same described herein and shown in the drawings represent only presently preferred embodiments of the invention. Indeed, various modifications and additions may be made to such embodiments without departing from the spirit and scope of the invention. For example, various different configurations, e.g., lengths, shapes, cross-sectional areas, etc., of the first tubular member and the cutter are contemplated. Also, those skilled in the art will appreciate that various different actuation means, e.g., pressure, vacuum, electrical, mechanical, hydraulic, etc. are suitable for use in the present invention. Thus, these and other modifications and additions may be implemented to adapt the present invention for a use in a variety of different applications.

What is claimed is:

1. A device for performing an anterior capsulotomy procedure, said device comprising:
   a) a body;
   b) an elongate tubular member extending from said body and having proximal and distal ends, said tubular member comprising a wall and also having a lumen formed generally therethrough, an opening being formed in the wall proximate the distal end, the distal end of said tubular member being closed;
   c) a cutter movably disposed within the lumen of said tubular member, said cutter having a blade formed thereon;
   d) a vacuum port in fluid communication with the lumen of said tubular member;
   e) an actuator for effecting movement of said cutter so as to move the blade across the opening formed in the wall of said tubular member;
   f) a form disposed within said tubular member proximate said opening about which a portion of an anterior capsule folds so as to increase the size of the opening cut in the anterior capsule by said cutter; and
   g) wherein the tubular member, the opening formed therein, and the form are configured to draw in and cut a sufficient portion of an anterior capsule to perform an anterior capsulotomy.

2. The device as recited in claim 1 wherein said tubular member comprises a generally flat lower surface and a bowed upper surface so as to reduce the cross-sectional area thereof and also so as to provide an enhanced vacuum seal about the opening formed in the wall of said elongate tubular member.

3. The device as recited in claim 1 wherein said actuator comprises:
   a) a diaphragm in mechanical communication with said cutter, said diaphragm defining an over-center device; and
   b) a pressure port in fluid communication with said diaphragm such that applying pressure to said pressure port effects movement of said cutter.

4. The device as recited in claim 3 wherein said actuator further comprises a wire interconnecting said diaphragm and said cutter, said wire configured to translate within said tube.

5. The device as recited in claim 3 wherein said actuator further comprises a rigid, hollow tube formed at a proximal end of the tube to said diaphragm and formed at a distal end of the tube to a wire, said wire effecting movement of said blade.

6. The device as recited in claim 1 further comprising a bend of between approximately 10 degrees and approximately 20 degrees formed in said tubular member to facilitate manipulation thereof.

7. The device as recited in claim 6 wherein said bend comprises a bend of approximately 15 degrees.

8. The device as recited in claim 1 wherein said form is configured to cooperate with the anterior capsule drawn into the tubular member to define a void for applying vacuum to the anterior capsule so as to hold the anterior capsule within said tubular member.

9. The device as recited in claim 1 wherein said form is shaped generally like a mushroom.

10. The device as recited in claim 1 further comprising a guide formed to said tubular member for limiting movement of said cutter generally to longitudinal movement through said tubular member and across said opening.

11. The device as recited in claim 10 wherein said guide comprises two tracks extending along at least a portion of said tubular member within which said cutter slides.

12. The device as recited in claim 1 wherein said cutter comprises:
   a) an upward bend formed therein proximate the blade thereof;
   b) a downward bend formed therein intermediate said upward bend and said blade; and
   c) wherein said upward bend and said downward bend cooperate to bias said blade downward so as to enhance cutting of an anterior capsule therewith.

13. A device for performing an anterior capsulotomy procedure, said device comprising:
   a) a body;
   b) an elongate tubular member extending from said body and having proximal and distal ends, said tubular member comprising a wall and also having a lumen formed generally therethrough, an opening being formed in the wall proximate the distal end, the distal end of said tubular member being closed;
   c) a cutter movably disposed within the lumen of said tubular member, said cutter having a blade formed thereon;
   d) a guide for limiting movement of said cutter generally to longitudinal movement through said tubular member and across said opening, said guide comprising two tracks extending along at least one portion of said tubular member within which said cutter slides;
   e) a vacuum port in fluid communication with the lumen of said tubular member;
   f) an actuator for effecting movement of said cutter so as to move the blade across the opening formed in the wall of said tubular member; and
   g) wherein the tubular member and the opening formed therein are configured to draw in and cut a sufficient portion of an anterior capsule to perform an anterior capsulotomy.

14. The device as recited in claim 13 wherein said tubular member comprises a generally flat lower surface and a bowed upper surface so as to reduce the cross-sectional area thereof and also so as to provide an enhanced vacuum seal about the opening formed in the wall of said elongate tubular member.

15. The device as recited in claim 13 wherein said actuator comprises:
   a) a diaphragm in mechanical communication with said cutter, said diaphragm defining an over-center device; and
   b) a pressure port in fluid communication with said diaphragm such that applying pressure to said pressure port effects movement of said cutter.

16. The device as recited in claim 15 wherein said actuator further comprises a wire interconnecting said diaphragm and said cutter, said wire configured to translate within said tube.

17. The device as recited in claim 15 wherein said actuator further comprises a rigid, hollow tube formed at a proximal end of the tube to said diaphragm and formed at a distal end of the tube to a wire, said wire effecting movement of said blade.

18. The device as recited in claim 13 further comprising a bend of between approximately 10 degrees and approximately 20 degrees formed in said tubular member to facilitate manipulation thereof.

19. The device as recited in claim 18 wherein said bend comprises a bend of approximately 15 degrees.

20. The device as recited in claim 13 further comprising a form disposed within said tubular member proximate said opening about which a portion of an anterior capsule folds so as to increase the size of the opening cut in the anterior capsule by said cutter.

21. The device as recited in claim 20 wherein said form is configured to cooperate with the anterior capsule drawn into the tubular member to define a void for applying vacuum to the anterior capsule so as to hold the anterior capsule within said tubular member.

22. The device as recited in claim 20 wherein said form is shaped generally like a mushroom.

23. The device as recited in claim 13 wherein said cutter comprises:
   a) an upward bend formed therein proximate the blade thereof;
   b) a downward bend formed therein intermediate said upward bend and said blade; and
   c) wherein said upward bend and said downward bend cooperate to bias said blade downward so as to enhance cutting of an anterior capsule therewith.

* * * * *